(12) United States Patent
Kuo

(10) Patent No.: US 7,476,100 B2
(45) Date of Patent: Jan. 13, 2009

(54) GUIDE APPARATUS AND METHODS FOR MAKING TOOTH POSITIONING APPLIANCES

(75) Inventor: Eric E. Kuo, Foster City, CA (US)

(73) Assignee: Align Technology, Inc., Santa Clara, CA (US)

( * ) Notice: Subject to any disclaimer, the term of this patent is extended or adjusted under 35 U.S.C. 154(b) by 619 days.

(21) Appl. No.: 11/131,018

(22) Filed: May 17, 2005

(65) Prior Publication Data

US 2006/0263738 A1    Nov. 23, 2006

(51) Int. Cl.
*A61C 3/00* (2006.01)
(52) U.S. Cl. ............................................ 433/6; 433/24
(58) Field of Classification Search .................. 433/2, 433/6, 24
See application file for complete search history.

(56) References Cited

U.S. PATENT DOCUMENTS 5,975,893 A * 11/1999 Chishti et al. .................. 433/6

* cited by examiner

*Primary Examiner*—Ralph A Lewis
(74) *Attorney, Agent, or Firm*—Klein, O'Neill & Singh, LLP

(57) ABSTRACT

A method for manipulating a three-dimensional model of a patient's teeth for making one or more tooth positioning appliances involves: forming at least one three-dimensional model of the patient's teeth; acquiring an initial digital data set representing at least part of the three-dimensional model; manipulating a digital model derived from the initial digital data set to move at least one tooth from an initial position to a first intermediate position; forming a first guide from the digital model with the at least one tooth in the first intermediate position; separating the at least one tooth from the three-dimensional model; placing the at least one tooth in the first guide in the first intermediate position; and securing the at least one tooth to the three-dimensional model in the first intermediate position. Guide apparatus and systems are also provided.

60 Claims, 8 Drawing Sheets

GUIDE APPARATUS AND METHODS FOR MAKING TOOTH POSITIONING APPLIANCES

BACKGROUND OF THE INVENTION

The invention relates generally to orthodontic and dental devices and systems and methods for making same. More specifically, the invention relates to guide apparatus, systems and methods for making tooth positioning appliances.

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. The brackets and bands are bonded to the patient's teeth using a suitable material, such as dental adhesive. Once the adhesive has set, the archwire is attached to the brackets by way of slots in the brackets. The archwire links the brackets together and exerts forces on them to move the teeth over time. Twisted wires or elastomeric O-rings are commonly used to reinforce attachment of the archwire to the brackets. Attachment of the archwire to the brackets is known in the art of orthodontia as "ligation" and wires used in this procedure are called "ligatures." The elastomeric O-rings are called "ties."

After the archwire is in place, periodic meetings with the orthodontist are required, during which the patient's braces are adjusted. Such adjustments include installing and bending different archwires having different force-inducing properties and replacing or tightening existing ligatures. Between orthodontic appointments, the patient may be required to wear supplemental appliances, such as elastic bands or headgear, to supply additional or extraoral forces.

Although conventional braces are effective, they are often a tedious and time consuming process requiring many visits to the orthodontist's office. Moreover, from a patient's perspective, they are unsightly and uncomfortable. Moreover, the archwire and ligatures which connect the brackets in a continuous network make brushing, flossing between the teeth and other dental hygiene procedures challenging, possibly contributing to the development of gingivitis, enamel decalcification and/or decay. Consequently, alternative orthodontic treatments are needed. In particular, it would be desirable to use appliances which can be removed by the patient during daily dental hygiene routines, while participating in athletic activities, or for cosmetic purposes.

A particularly promising approach relies on the use of elastic positioning appliances for realigning teeth. Such appliances comprise a thin shell of elastic material that generally conforms to a patient's teeth but is slightly out of alignment with the initial tooth configuration. Placement of the elastic positioner over the teeth applies controlled forces in specific locations to gradually move the teeth into the new configuration. Repetition of this process with successive appliances comprising new configurations eventually moves the teeth through a series of intermediate configurations to a final desired configuration. Various systems, methods and apparatus for moving teeth with such appliances are described in numerous patents assigned to the assignee of the present application, such as U.S. Pat. Nos. 5,975,893; 6,183,248; 6,210,162; 6,217,325; 6,227,851; 6,227,850; 6,299,440; 6,309,215; 6,318,994; 6,371,761; 6,386,864; 6,386,878; 6,390,812; D457,638S; U.S. Pat. Nos. 6,394,801; 6,398,548; 6,406,292; 6,409,504; 6,450,807; 6,454,565; 6,457,972; 6,463,344; 6,471,511; 6,485,298; 6,488,499; 6,497,574; 6,499,997; 6,514,074; 6,524,101; 6,554,611; 6,572,372; 6,582,227; 6,582,229; 6,602,070; 6,607,382; 6,621,491; 6,626,666; 6,629,840; 6,633,789; 6,665,570; 6,682,346; 6,685,469; 6,685,470; 6,688,886; 6,699,037; 6,705,861; 6,705,863; 6,722,880; 6,726,478; 6,729,876; 6,761,560; 6,767,208; 6,783,360; 6,783,604; 6,786,721; 6,790,035; 6,802,713; 6,814,574; and 6,830,450; all of which are incorporated herein by reference and are referred to below as "the incorporated references."

One method for manufacturing tooth positioning appliances, described more fully in the incorporated references, involves taking an impression of the patient's teeth, scanning the impression to provide an initial digital data set representing the teeth in their pre-treatment positions, manipulating the digital data to provide intermediate and final digital data sets representing treatment positions for moving the teeth, using the data sets to create positive molds of the appliances, and making appliances as negatives of the positive molds. Variations of such methods may involve directly scanning the patient's teeth, creating a solid model of the teeth and scanning the model, manipulating such a solid model, and many other variations described in the incorporated references. In some techniques, the positive molds are created using a rapid prototyping method, such as stereolithography. Appliances are then made by thermoforming or otherwise forming a plastic material over the molds and separating and trimming the plastic to produce the appliances. Although such manufacturing methods work quite well and are often optimal for producing tooth moving appliances, alternative manufacturing methods that may be more efficient, less expensive, require less material or manual input and the like are continually being sought.

One alternative method for making tooth moving appliances involves first forming a physical, three-dimensional model of the patient's upper or lower teeth. One or more of the teeth are then separated from the model, such as by cutting, and moved to a desired intermediate or final position on the model. The moved tooth or teeth are then secured in place on the model in its/their new positions, and a plastic or similar material is formed over the model with the moved teeth. The formed plastic is then trimmed and removed from the model to produce an appliance. One or more teeth can then be separated from the model again, moved to new positions and secured, and a second appliance may be formed over the model. This can be repeated to form as many appliances, or sets of upper and lower appliances, as desired. In an alternative version, the model may be manipulated to a first configuration, a copy of the model may be made, and an appliance may be made from the copy. The original model may be moved to a second configuration, a copy made, and a second appliance made, and so on. One advantage of such methods is that an inexpensive material, such as dental plaster, may be used to form the model (or models) of the patient's teeth, and such a material and process will typically be less expensive than certain rapid prototyping processes, such as stereolithography, which produces a separate positive mold of hardened resin for each appliance to be manufactured. Such methods of manually manipulating a solid model have inherent drawbacks, however, in that the teeth separated from the model are placed in their new positions on the model by hand and by approximation. These manipulations require a great deal of skill and experience, which may lead to suboptimal results for the patient and may also make mass production of appliances very difficult, if not impossible.

Therefore, it would be desirable to develop alternative methods, systems and apparatus for manipulating physical tooth models and for making tooth moving appliances. Such methods, systems and apparatus would ideally provide for precision in model manipulation and, thus, in production of appliances. Such methods, systems and apparatus would also ideally provide for appliance manufacture at reduced cost as compared to currently available, more precise methods. For example, such methods, systems and apparatus may require less material or human input. At least some of these objectives will be met by the present invention.

BRIEF SUMMARY OF THE INVENTION

In one aspect of the present invention, a method for manipulating a three-dimensional model of a patient's teeth for making one or more tooth positioning appliances involves: forming at least one three-dimensional model of the patient's teeth; acquiring an initial digital data set representing at least part of the three-dimensional model; manipulating a digital model derived from the initial digital data set to move at least one tooth from an initial position to a first intermediate position; forming a first guide from the digital model with the at least one tooth in the first intermediate position; separating the at least one tooth from the three-dimensional model; placing the at least one tooth in the first guide in the first intermediate position; and securing the at least one tooth to the three-dimensional model in the first intermediate position.

In various embodiments, three-dimensional models of the patient's teeth may include a model of the patient's upper teeth, lower teeth, a bite registration model, or some combination thereof. Forming the three-dimensional model, in some embodiments, involves taking at least one impression of the patient's upper teeth, lower teeth, or both, depositing a material into the impression, allowing the material to harden to form the three-dimensional model, and removing the three-dimensional model from the impression. For example, depositing the material may involve depositing plaster, stone, plastic or polymeric material into the impression.

In some embodiments, acquiring the initial digital data set involves scanning the three-dimensional model, the patient's teeth and/or an impression of the patient's teeth to produce one or more digital scans. Alternatively, the initial digital data set may be acquired by receiving one or more digital scans from a third party source. In either case, the digital scan(s) may be acquired using a scanner such as but not limited to a computed tomography, magnetic resonance imaging, X-ray, laser, structured light, spectral light or destructive scanner.

Optionally, manipulating the digital model may involve moving a plurality of teeth from initial positions to first intermediate positions. Also optionally, the method may include reshaping at least one tooth on the digital model to facilitate repositioning of the tooth.

Forming the first guide may involve using a computer to direct a fabricating machine to form the guide, based on the manipulated digital model. For example, using the computer to direct the fabricating machine may involve directing a milling machine to mill a plurality of recesses into a piece of material, each recess formed to receive at least a portion of a tooth of the three-dimensional model. Alternatively, using the computer to direct the fabricating machine may involve directing a rapid prototyping machine to build up the guide from a material, the guide having a plurality of recesses, each recess formed to receive at least a portion of a tooth of the three-dimensional model. Examples of such rapid prototyping machines include, for example, stereolithography, laminate object manufacturing and fused deposition modeling machines.

In some embodiments, at least one of the separating, placing and securing steps are performed by a robot or other automated machine. Such embodiments may optionally also include the steps of placing at least one reference jig on the three-dimensional model after the forming step and removably attaching the three-dimensional model to an automated cutting machine, using the jig as a reference. The cutting machine then performs the separating step. Another optional step in such embodiments includes removably attaching the three-dimensional model to an automated tooth placing machine, using the jig as a reference. The tooth placing machine then performs the placing step.

Securing the separated tooth (or teeth) back onto the three-dimensional model may be achieved in a number of different ways and with a number of different substances, such as but not limited to wax, adhesive, resin, silicone or stone compounds. In many embodiments, multiple teeth are separated and moved to new positions using the guide. In such embodiments, the method may further involve labeling the teeth that are separated from the three-dimensional model to indicate positions in which they should be placed in the guide. Typically, such methods will further include marking the guide to match each labeled tooth with a corresponding position in the guide. Optionally, the method may also include reducing the size of at least one tooth separated from the three-dimensional model to facilitate repositioning of the tooth. Another optional step involves placing one or more grooves or other surface markings on at least one separated tooth to facilitate securing of the tooth back onto the three-dimensional model. Such a method may further include placing one or more additional grooves or other surface markings on the three-dimensional model to further facilitate the securing step.

In some embodiments, the method also includes removing the three-dimensional model from the guide with the at least one tooth secured to it in the first intermediate position and forming a first tooth positioning appliance over the three-dimensional model. Optionally, the method may further involve, after the removing step, forming a first intermediate model from the three-dimensional model, with the first tooth positioning appliance being formed over the first intermediate model. In either case, the method may involve forming the first tooth positioning appliance by thermoforming a plastic material over the three-dimensional model or first intermediate model. Other appliance manufacturing techniques for making the appliance over the model may alternatively be used.

In some embodiments, the method also includes: manipulating the digital model to move the at least one tooth from the first intermediate position to a second intermediate position; forming a second guide from the digital model with the at least one tooth in the second intermediate position; separating the at least one tooth from the three-dimensional model; placing the at least one tooth in the guide in the second intermediate position; and securing the at least one tooth to the three-dimensional model in the second intermediate position. The method may then further involve forming a first tooth positioning appliance over the three-dimensional model after the first securing step and forming a second tooth positioning appliance over the three-dimensional model after the second securing step. Optionally, the method may include forming, after the first securing step, a first intermediate model from the three-dimensional model, and forming, after the second securing step, a second intermediate model from the three-dimensional model. The method may then include forming first and second tooth positioning appliances over the first and second intermediate models.

In various embodiments, the steps described above may be repeated as many times as desired to produce three, four, five, thirty or as many guides and appliances as needed to move the patient's teeth in a desired way. In some embodiments, each guide or appliance in a series of guides or appliances moves the same teeth as the other guides or appliances, and the teeth are moved incrementally from guide to guide or from appliance to appliance. In another embodiment, each guide or appliance may move a different tooth or set of teeth from the tooth/teeth moved by the other guides or appliances. And in yet other embodiments, guides and appliances may move teeth in a combination of ways. For example, a first guide and a first appliance may move a first tooth from an initial position to a new position. A second guide and a second appliance may then be used to move a second tooth from an initial position to a new position. A third guide and a third appliance may be subsequently used to move a third tooth from an initial position to a new position and may also be used to move the first and second teeth to new positions. Any desired combination may be achieved by the guides and appliances of the present invention.

In another aspect of the present invention, a method for making a tooth positioning appliance for repositioning a patient's teeth involves: forming a first guide from a digital model of the patient's teeth; separating at least one tooth from a three-dimensional model of the patient's teeth; placing the at least one tooth in the first guide, wherein the first guide repositions the at least one tooth relative to the rest of the three-dimensional model from an initial position to a first position; securing the at least one tooth to the three-dimensional model in the first intermediate position; and forming a first tooth positioning appliance over the three-dimensional model with the at least one tooth in the first position. Any of the steps, features or variations described above may be applied to this method for making a tooth position appliance. Furthermore, the method may be repeated as many times as desired, in various embodiments, to provide multiple guides and appliances.

In another aspect of the present invention, a method for making a guide for positioning one or more teeth on a three-dimensional model of a patient's teeth involves: forming at least one three-dimensional model of the patient's teeth; acquiring an initial digital data set representing at least part of the three-dimensional model; manipulating a digital model derived from the initial digital data set to move at least one tooth from an initial position to a first position; and forming a first guide from the digital model, wherein the first guide is configured to receive the at least one moved tooth and at least one other tooth of the three-dimensional model so as to reposition the at least one tooth to the first position relative to the three-dimensional model. Again, any of the steps, features or variations described above may be applied to this method for making a guide, and the steps may be repeated to provide as many guides as desired.

In another aspect of the present invention, a method for making a plurality of tooth positioning appliances for repositioning a patient's teeth includes: providing a series of guide-forming tooth models, based on a series of digital data sets derived from the patient's teeth; forming a series of guides from the guide-forming models; separating at least one tooth from a 3D model of the patient's teeth; placing the at least one tooth in a first guide of the set of guides, wherein the first guide repositions the at least one tooth relative to the rest of the 3D model from an initial position to a first position; securing the at least one tooth to the 3D model in the first intermediate position; forming a first tooth positioning appliance over the 3D model with the at least one tooth in the first position; and repeating the separating, placing, securing and forming steps as many times as desired to provide a plurality of appliances. Any of the features or variations described in terms of the methods above may be applied, in various embodiments.

In yet another aspect of the present invention, an apparatus for manipulating a three-dimensional model of a patient's teeth for making one or more tooth positioning appliances includes a guide fabricated by a computer-directed fabrication machine and having a plurality of recesses, each recess shaped to receive at least a portion of a tooth of the model. At least one of the recesses is shaped to reposition a tooth separated from the model from an initial position to a first position, and the at least one recess shaped to reposition the tooth is shaped according to instructions from a manipulated digital model of the patient's teeth.

In some embodiments, the guide comprises a three-dimensional bite pattern guide representing a bite pattern of the patient's upper teeth. Alternatively, the guide may comprise a three-dimensional bite pattern guide representing a bite pattern of the patient's lower teeth or of both the upper and lower teeth. In alternative embodiments, the guide comprises a surface pattern shaped to receive one or more surfaces of the at least one tooth and of at least one additional tooth of the three-dimensional model. For example, the guide may comprise a facial surface pattern shaped to receive facial surfaces of the teeth, a buccal surface pattern shaped to receive buccal surfaces of the teeth, a lingual surface pattern shaped to receive lingual surfaces of the teeth, or the like.

In various embodiments, the guide may be comprised of any suitable material, such as but not limited to plastic, polymer, metal, plaster, wax or paper. In some embodiments, the guide is milled from a solid piece of material, while in other embodiments, the guide is built in multiple layers of material. Oftentimes, a plurality of the recesses on a guide are shaped to reposition a plurality of teeth on the three-dimensional model, each recess configured to reposition one of the teeth. Optionally, the guide may further include at least one reference marking corresponding to at least one reference marking on at least one tooth of the three-dimensional model, the reference marking allowing a user to determine where the at least one tooth should be placed in the guide. A guide may also include at least one reference label for allowing a user to determine where the guide should be located relative to others in a series of guides. In some embodiments, the guide is configured to reposition the at least one tooth in such a way as to allow a tooth positioning appliance to be formed over the three-dimensional model.

In another aspect of the present invention, a system for manipulating a three-dimensional model of a patient's teeth for making one or more tooth positioning appliances includes a first guide having a plurality of recesses to receive teeth of the model, wherein at least one recess is configured to reposition a tooth of the model from an initial position to a first position, and at least a second guide having a plurality of recesses to receive teeth of the model, wherein at least one recess is configured to reposition a tooth of the model from the first position to the second position. The guides are fabricated by a computer-directed fabrication machine, and the at least one recess of each guide that is shaped to reposition the tooth is shaped according to instructions from a manipulated digital model of the patient's teeth. Each guide of the system may have any of the features, and may be made using any of the methods, described above. The system may include anywhere from two to thirty or even more than thirty guides or sets of guides for making any number of appliances or sets of appliances.

In another aspect of the present invention, a system for manipulating a three-dimensional model of a patient's teeth for making one or more tooth positioning appliances includes a first guide having a plurality of recesses to receive the teeth of the model, wherein at least one recess is configured to reposition a first tooth of the model from an initial position to a new position, and at least a second guide having a plurality of recesses to receive the teeth of the model, wherein at least one recess is configured to reposition a second tooth of the model from an initial position to a new position. The guides are fabricated by a computer-directed fabrication machine, and the at least one recess of each guide that is shaped to reposition the tooth is shaped according to instructions from a manipulated digital model of the patient's teeth. As with the system described above, this system may include anywhere from two to thirty or even more than thirty guides or sets of guides for making any number of appliances or sets of appliances.

In another aspect of the present invention, a system for making tooth positioning appliances includes: at least one three-dimensional model of a patient's teeth, with at least one tooth of each model separated from the model; a first guide having a plurality of recesses to receive teeth of the model, wherein at least one recess is configured to reposition the at least one separated tooth of the model from an initial position to a first position; at least a second guide having a plurality of recesses to receive teeth of the model, wherein at least one recess is configured to reposition the separated tooth from the first position to a second position; and material for forming a first tooth positioning appliance over the three-dimensional model when the separated tooth is in the first position and at least a second tooth positioning appliance over the three-dimensional model when the separated tooth is in the second position. The guides are fabricated by a computer-directed fabrication machine, and wherein the at least one recess shaped to reposition the tooth is shaped according to instructions from a manipulated digital model of the patient's teeth.

Optionally, the system may further comprise a robot or other automated machine for separating teeth from the three-dimensional model, placing teeth in the guide, securing teeth to the three-dimensional model, trimming the appliances and/or removing the appliances from the model.

In yet another aspect of the invention, a system for making tooth positioning appliances may include: at least one three-dimensional model of a patient's teeth, with at least one tooth of each model separated from the model; a first guide having a plurality of recesses to receive teeth of the model, wherein at least one recess is configured to reposition the at least a first separated tooth of the model from an initial position to a new position; at least a second guide having a plurality of recesses to receive teeth of the model, wherein at least one recess is configured to reposition at least a second separated tooth of the model from an initial position to a new position; and material for forming a first tooth positioning appliance over the three-dimensional model when the first separated tooth is in its new position and at least a second tooth positioning appliance over the three-dimensional model when the second separated tooth is in its new position. Again, the guides are fabricated by a computer-directed fabrication machine, and the at least one recess of each guide that is shaped to reposition the tooth is shaped according to instructions from a manipulated digital model of the patient's teeth.

Further aspects and embodiments of the present invention are described in greater detail below, with reference to the attached drawing figures.

DETAILED DESCRIPTION OF THE INVENTION

Methods, apparatus and systems are provided for manipulating physical models of teeth, typically for the purpose of making one or more tooth positioning appliances. The word "physical" is meant to distinguish from computer models of teeth, although many embodiments of the method involve providing and manipulating both computer tooth models and physical tooth models. The methods, apparatus and systems described below provide a technique for manipulating physical tooth models for producing tooth moving appliances, which may provide a number of advantages.

Figure 1A:
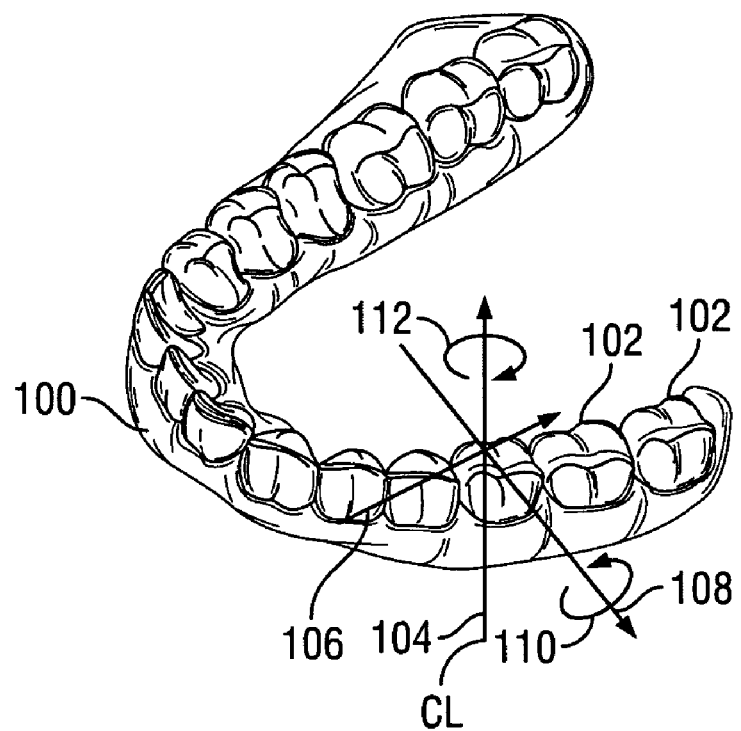
FIG. 1A illustrates a patient's jaw and provides a general indication of how teeth may be moved.

Referring now to FIG. 1A, a representative jaw 88 includes sixteen teeth, at least some of which may be moved from an initial tooth arrangement to a final tooth arrangement using one or more tooth moving appliances. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline. Thus, all possible free-form motions of the tooth can be performed.

Figure 1B:
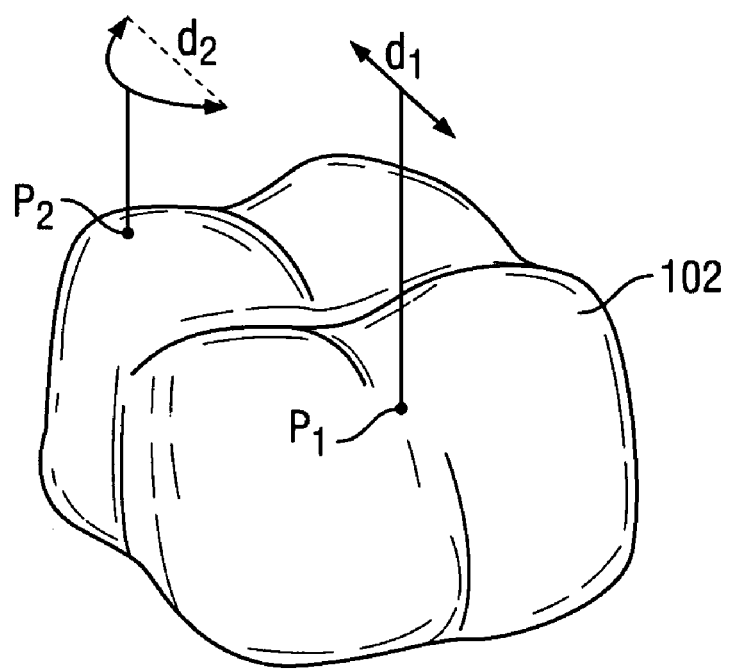
FIG. 1B illustrates a single tooth from FIG. 1A and defines how tooth movement distances are determined.

Referring now to FIG. 1B, the magnitude of any tooth movement is defined in terms of the maximum linear translation of any point P on a tooth 102. Each point $P_i$ will undergo a cumulative translation as that tooth is moved in any of the orthogonal or rotational directions defined in FIG. 1A. That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point $P_2$ may travel along an arcuate path, resulting in a final translation $d_2$. In many situations, the maximum permissible movement of a point $P_i$ in any particular tooth is defined as the maximum linear translation of that point $P_i$ on the tooth that undergoes the maximum movement for that tooth in any treatment step.

Figure 1C:
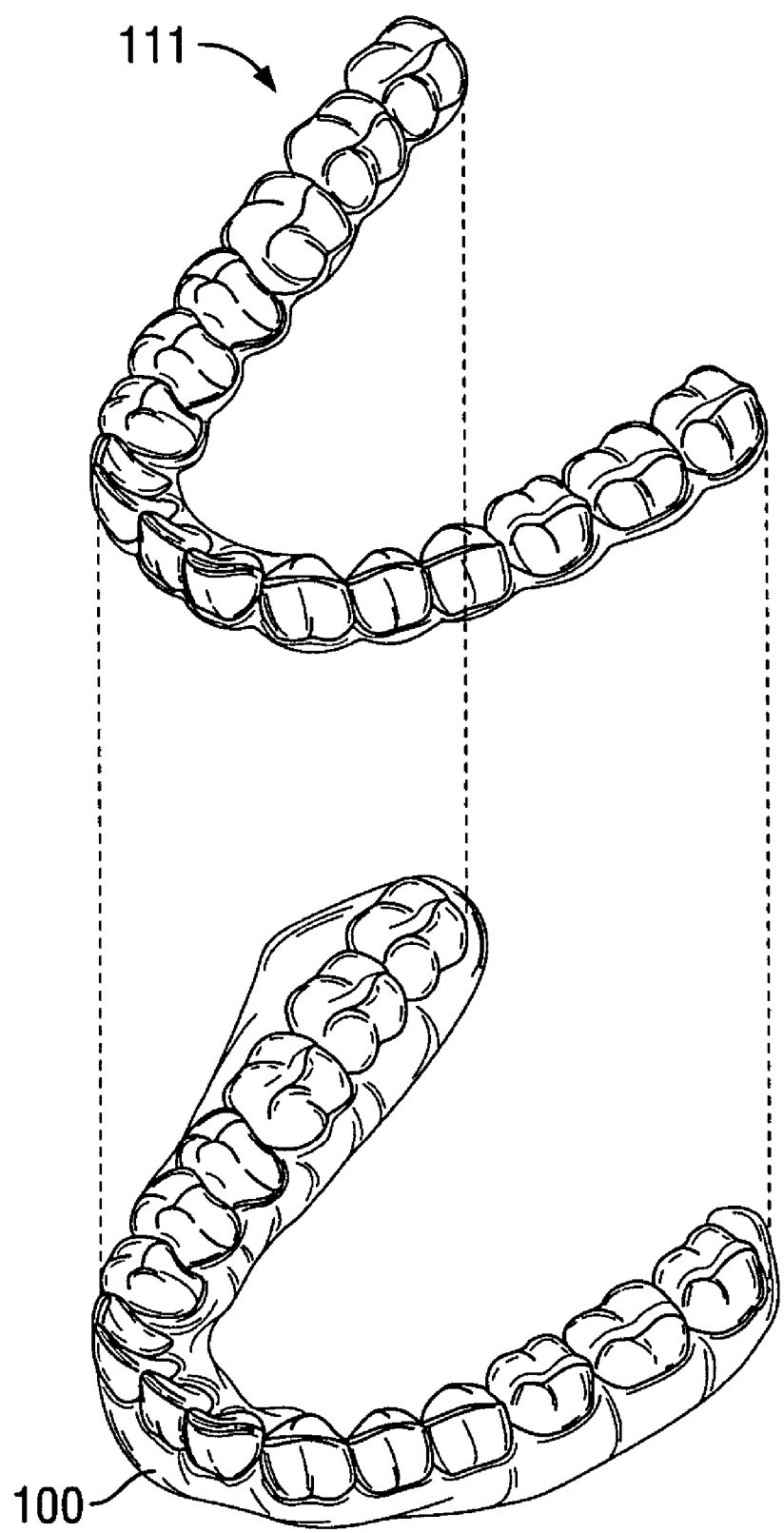
FIG. 1C illustrates the jaw of FIG. 1A together with a tooth positioning appliance.

Referring now to FIG. 1C, one tool for incrementally repositioning the teeth in a patient's jaw comprises a clear, plastic, tooth moving (or "tooth positioning") appliance 111. Examples of such appliances are described in greater detail in the incorporated references. The appliance 111 typically comprises a polymeric shell having a cavity shaped to receive and resiliently reposition teeth from one tooth arrangement to another tooth arrangement. The polymeric shell 111 typically fits over all teeth present in the upper or lower jaw. Often, only some of the teeth will be repositioned while others will provide a base or anchor region for holding the repositioning appliance 111 in place as it applies the resilient repositioning force against the tooth or teeth to be repositioned. In complex cases, many or most of the teeth will be repositioned at some point during the treatment. In such cases, the teeth which are moved can also serve as a base or anchor region for holding the repositioning appliance. The gums and the palette also serve as an anchor region in some cases, thus allowing all or nearly all of the teeth to be repositioned simultaneously.

The polymeric appliance 111 of FIG. 1C is preferably formed from a thin sheet of a suitable elastomeric polymeric, such as Tru-Tain 0.03 in. thermal forming dental material, marketed by Tru-Tain Plastics, Rochester, Minn. 55902. In many cases, no wires or other means are provided for holding the appliance in place over the teeth. In some cases, however, it is necessary to provide individual attachments on the teeth with corresponding receptacles or apertures in the appliance 111 to enable it to apply forces that would not be possible or would be difficult to apply in the absence of such attachments. Again, for further details on such elastic appliances 111 and methods, systems and apparatus for their manufacture and use, reference may be made to the incorporated references.

Figure 2:
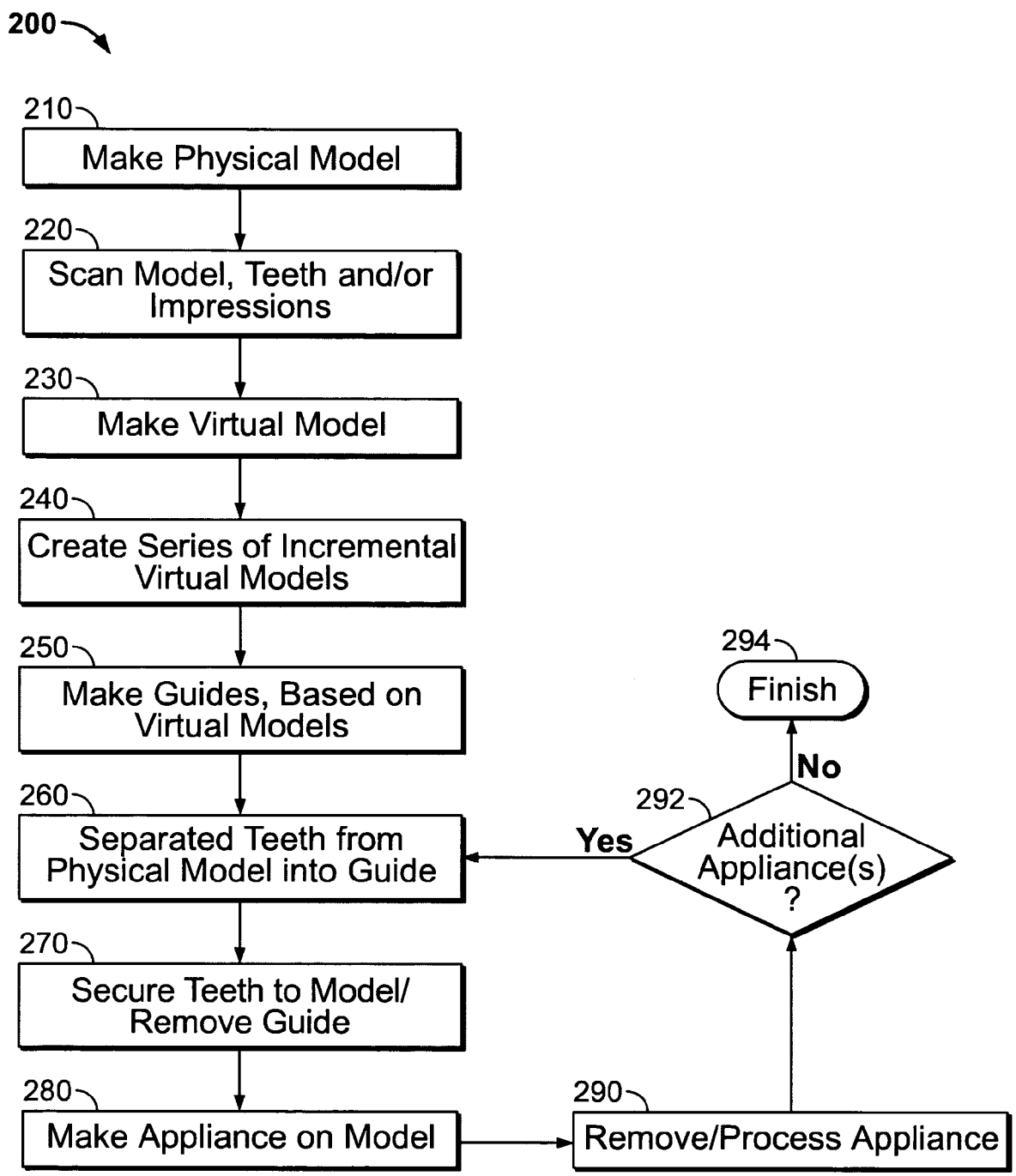
FIG. 2 is a block diagram illustrating a method for producing one or more tooth positioning appliances, according to one embodiment of the present invention.

With reference now to FIG. 2, one embodiment of a method 200 for making tooth moving appliances is described. As will be described further below, the method 200 is but one embodiment, and alternative embodiments may include additional steps, fewer steps and/or different steps in the place of one or more shown in FIG. 2. Therefore, the method 200 of FIG. 2 is provided primarily for exemplary purposes and should not be interpreted to limit the scope of the inventive method.

That being said, the exemplary method 200 may first involve making a physical model of a patient's teeth 210. Such a model (or set of models) may be made by any conventional tooth modeling technique or any technique discovered in the future. In one embodiment, for example, making the model 210 involves making models of the patient's upper set of teeth, lower set of teeth and bite registration of the upper teeth with the lower teeth. In one well known method, impressions of the patient's upper and lower teeth are taken in a common impression material, such as polyvinylsiloxane (PVS) or alginate, and an impression is also taken of the patient's bite pattern. Dental plaster or "stone" may then be poured into the upper and lower impressions and allowed to harden, to form upper and lower tooth models. One well known technique for preparing plaster casts of a patient's teeth is described in Graber, *Orthodontics: Principle and Practice*, Second Edition, Saunders, Philadelphia, 1969, pp. 401-415, although any other suitable modeling technique may be used. In some embodiments, for example, the model may be made of plastic or some material other than plaster.

Before, after and/or during the model making process 210, one or more scans are taken 220 of the patient's teeth, one or more models of the patient's teeth, one or more impressions of the patient's teeth, or some combination thereof. Any suitable scanning technique (or a combination of techniques) may be used, such as but not limited to X-ray, three dimensional X-ray, laser, computed tomography (CT), magnetic resonance imaging (MRI), structured light, spectral light and/or destructive scanning techniques.

Once scans are acquired 220, if they are not already in the form of digital data, they may be converted into digital data. This digital data is then used to create one or more virtual (computerized) models of the patient's teeth 230. Many details of such a virtual tooth modeling process and model manipulation are described in the incorporated references. Typically, an initial digital data set (IDDS) representing an initial tooth arrangement is obtained. The IDDS represents the patient's teeth in their positions before treatment. The IDDS produced by the scanner may be presented in any of a variety of digital formats to ensure compatibility with the software used to manipulate images represented by the data. In addition to the 3D image data gathered by scanning the exposed surfaces of the teeth 220, a user may wish to gather data about hidden features, such as the roots of the patient's teeth and the patient's jaw bones. This information may be used to build a more complete model of the patient's dentition and to show with more accuracy and precision how the teeth will respond to treatment. For example, information about the roots allows modeling of all tooth surfaces, instead of just the crowns, which in turn allows simulation of the relationships between the crowns and the roots as they move during treatment. Information about the patient's jaws and gums also enables a more accurate model of tooth movement during treatment. For example, an X-ray of the patient's jaw bones can assist in identifying any loose teeth, and an MRI can provide information about the density of the patient's gum tissue. Moreover, information about the relationship between the patient's teeth and other cranial features allows accurate alignment of the teeth with respect to the rest of the head at each of the treatment steps. Data about these hidden features may be gathered from many sources, including 2D and 3D X-ray systems, CT scanners, and magnetic resonance imaging (MRI) systems.

As described more fully in the incorporated references, the virtual model(s) of the patient's teeth (the IDDS) may be manipulated 240 to create a final digital data set (FDDS), which represents a desired configuration for the patient's teeth at the end of treatment, and one or more intermediate digital data sets (INTDDS), representing incremental changes in the configurations of the teeth to get from the IDDS to the FDDS. Such manipulations 240 may be generated automatically by computer software, by manual manipulating using a computer having a suitable graphical user interface (GUI) and software appropriate for viewing and modifying the images, or by some combination thereof. In manipulating virtual models of teeth 240, any number of teeth may be moved, from just one tooth to as many teeth as practicable. In some embodiments, one or more teeth will be virtually shaved or reshaped to allow for the desired movement, and such reshaping will then be replicated later in the physical tooth model and the patient's actual teeth.

Once the patient's teeth and movements of teeth are modeled virtually 240, one or more guides may be made 250, based on the virtual models. Such guides each include multiple cavities or recesses into which teeth on a physical tooth model fit. As described further below, the cavities may conform to a bite pattern of the teeth or to facial, buccal, lingual or other surfaces of the teeth. The guides are first designed virtually, and the computer then directs one or more automated devices to make the guides. For example, in one embodiment the computer directs a rapid prototyping machine, such as a stereolithography machine, to make multiple guides by hardening a resin material. Other examples of rapid prototyping machines that may be used include laminate object manufacturing and fused deposition modeling machines. In another alternative embodiment, CAD-CAM machining is used to direct a milling machine to mill the guides out of solid pieces of material. Any other suitable computer-directed fabrication process may be used. Furthermore, any desired number of guides may be used. In one embodiment, for example, it may be desired to move only upper teeth of a patient and only in one step, and in such a case only one guide may be required. In another embodiment, upper and lower teeth may be moved through multiple stages of treatment, thus utilizing multiple sets of guides.

As described further below, each guide typically has at least one marking and more typically a plurality of markings. One marking, for example, may indicate where the guide should reside in a series of guides. Other markings typically include numbers or other markings to indicate where specific teeth from a tooth model should be placed in the guide. Such markings may be automatically or manually assigned, using the computer models of the guides, and the computer may then direct the guide-making machine to make the markings. Markings may be applied using any suitable technique, such as by laser printing or by applying surface features to the guides.

Before, during or after the guide(s) are being fabricated 250, one or more teeth are separated from the physical model (or models) of the patient's teeth. This separation is typically accomplished by cutting, using a saw or any known or hereafter discovered device or technique for cutting teeth from a tooth model. Typically, the separated teeth are numbered or marked in some way to indicate where they will be placed in the guide (or guides). Such markings may be made by any suitable method, such as manually marking or marking with a machine, such as a laser.

Once separated and marked, the separated teeth are then placed into a guide 260, generally a first in a series of guides. The separated teeth are then attached and secured to the tooth model 270, either with adhesive or by any other suitable means. In one embodiment, a commonly used holding compound is used to secure the teeth to the model. The holding compound may also be used to fill any voids, recreate gum tissue on the model and/or the like. Other substances used to the secure the teeth to the model may include, but are not limited to, wax, resin, silicone, stone compounds and/or other adhesives. During the securing process, at least one of the non-separated teeth of the model resides in an additional recess of the guide. In some embodiments, all additional teeth reside in additional recesses. The additional recesses allow the non-separated teeth to be registered with the separated teeth.

Any or all of the steps of cutting the teeth from the model, placing the teeth in the guides and securing the teeth to the model may be performed by one or more robotic machines or other automated machines. For example, a robotic arm with a saw tool and controlled by computer may be used for cutting the teeth from the patient's tooth model. The same or another robotic arm may then be used to place the separated teeth in the guide. And another robotic arm (or the same arm) may be used to apply adhesive to separated teeth to reattach them to the model. The same or another robotic arm may also be used to trim an appliance made on the model. In some embodiments, the model will include one or more jigs, registration attachments, features, markings or the like, for registering the model with a robotic apparatus or system. In alternative embodiments, any or all of the separating, placing and attaching steps may be performed by hand.

Once the separated teeth are reattached to the model 270, using the guide and any adhesive or other mechanism for attachment, the guide and model are separated, and an appliance is made on the model 280. Alternatively, the model may be used as a "master" model, from which a copy is made, and the appliance may be made on the copy. The copy may be made, for example, by taking an impression of the master and making the copy from the impression. Any suitable method may be used to form the appliance on the model, such as thermoforming an elastic material over the model. In one embodiment, after a material is thermoformed over the model, material extending over the gum line is cut off, typically by a CAD-CAM device. Again, in some embodiments this cutting (or "trimming") process may be performed by a robot or other automated machine.

Next, the appliance is removed from the model 290 and, in some cases, processed further, such as by sanding rough edges, washing and/or adding features to the appliance manually or via machine. If additional appliances are desired 292, one or more teeth may again be separated from the master model and placed in a next guide, the teeth may be reattached to the model, and another appliance may be made. If no additional appliances are needed, then the process is finished 294. In one embodiment, where copies of the master model are made, it may be most efficient to make all the desired copies of the master model before making any appliances. In alternative embodiments, an appliance may be made from each copy before making another copy, or some number of appliances may be made from some number of copies before making additional copies. Any suitable combination may be used.

As mentioned above, in various embodiments of the method just described, a number of steps may be added, eliminated or altered in some way, and/or the order of steps may be changed, without departing from the scope of the invention.

Figure 2A:
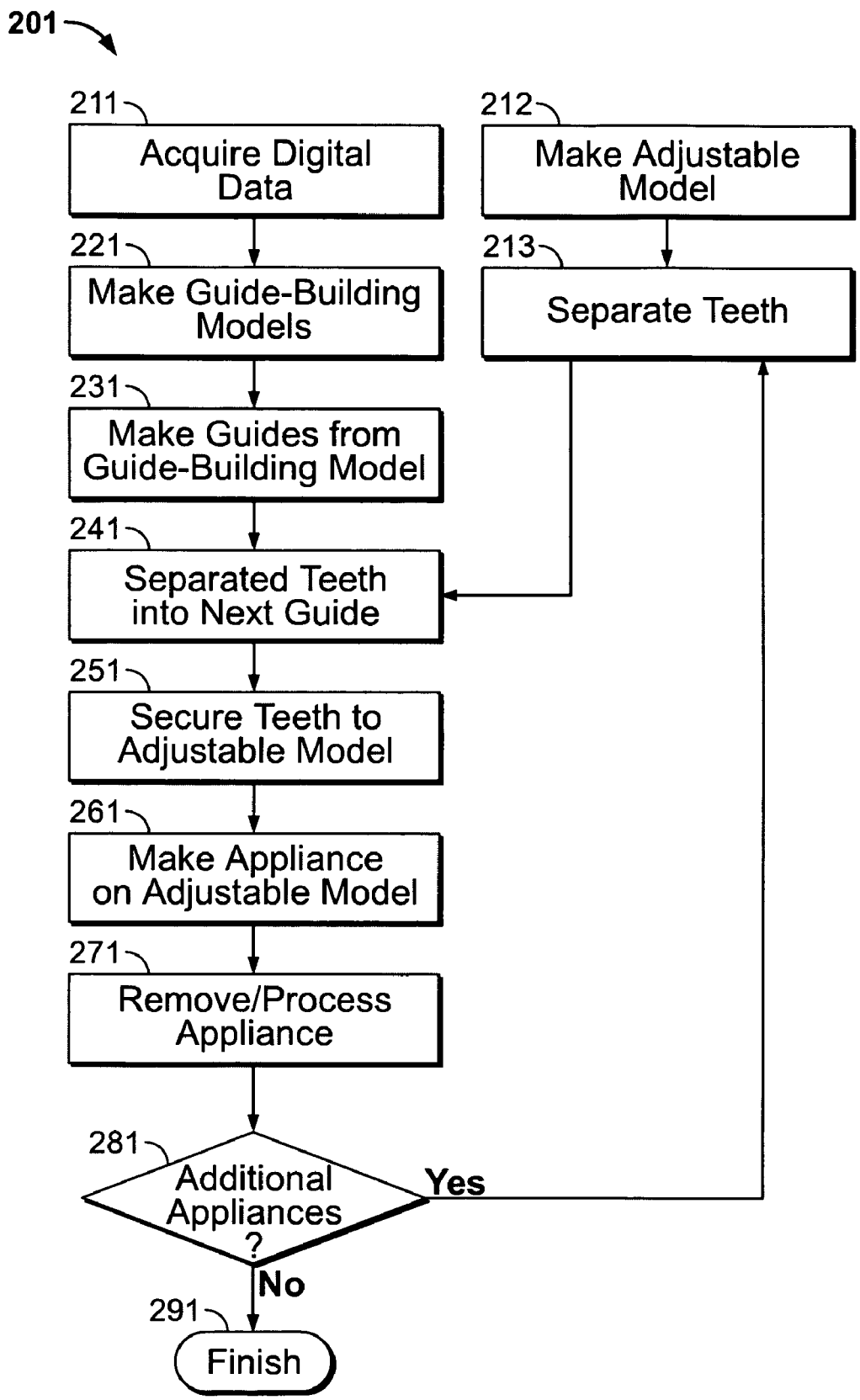
FIG. 2A is a block diagram illustrating a method for producing one or more tooth positioning appliances, according to an alternative embodiment of the present invention.

Referring now to FIG. 2A, an alternative embodiment of a method 201 for making tooth moving appliances is shown. The method 201 involves acquiring digital data 211 representing a patient's teeth and tooth movement of at least one tooth through at least one movement. Such data may be acquired by any of a number of different scanning techniques, as described more fully above, and may include any number of IDDS, INTDDS and/or FDDS or the like. In one embodiment, the data includes a series of 3D virtual models of the patient's teeth, moving from an initial configuration to a final configuration, with one or more steps in between. In various embodiments, any suitable digital data may be used.

Before, after or during digital data acquisition 211, one or more adjustable (or "3D") models of the patient's teeth are made 212, and one or more teeth too be repositioned on the model are separated from the model 213.

The digital data is used to make multiple guide-building models 221. For example, in one embodiment the data may direct a rapid prototyping machine, such as a stereolithography machine, to form the series of guide-building models by hardening a resin material. Multiple guides may then be made from the guide-building models 231. The guides may be made from the guide-building models by any suitable means, such as but not limited to curing a rigid material using heat, cold, chemical reaction, or light activation, forming the cured material over a guide-building model, and allowing the material to set.

Separated teeth from the 3D adjustable model may then be placed in a first guide in a series of guides 241. The teeth are then secured to the 3D model 251, an appliance is made over the 3D model 261, and the appliance is removed 271. If additional appliances are desired 281, the steps of separating teeth 213, placing teeth in the next guide 241, securing the teeth to the model 251, making an appliance 261 and removing the appliance 271 may be repeated as many times as desired. When no more appliances are desired, the method is finished 291. In a variation on this method, a copy model may be made from the original 3D model after each step of securing the teeth to the model 251, and the appliances may be made on the copy models. In various embodiments of this method, any of the features and variations described for methods above may be implemented.

Figure 3A:
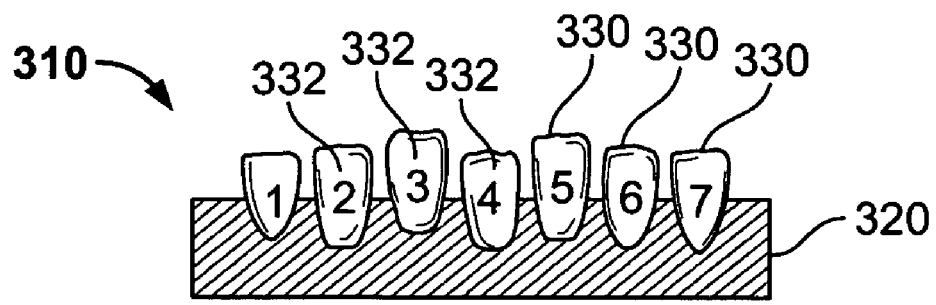
FIGS. 3A-3E are diagrammatic representations showing a method for manipulating a tooth model using a guide, according to one embodiment of the present invention.

With reference now to FIGS. 3A-3E, one embodiment of a method for manipulating a model of a patient's teeth is shown. As shown in FIG. 3A, a tooth model 310 may include a base 320 and multiple teeth 330. Although FIG. 3A is diagrammatic in nature, the model 310 is typically made from an impression of the patient's teeth (upper or lower), so that the base 320 has the shape of the patient's gum tissue. During or after the model 310 is made, the teeth 330 may labeled with numbers 332 or other markings, so that they may be registered with the guide in a later step.

Figure 3B:
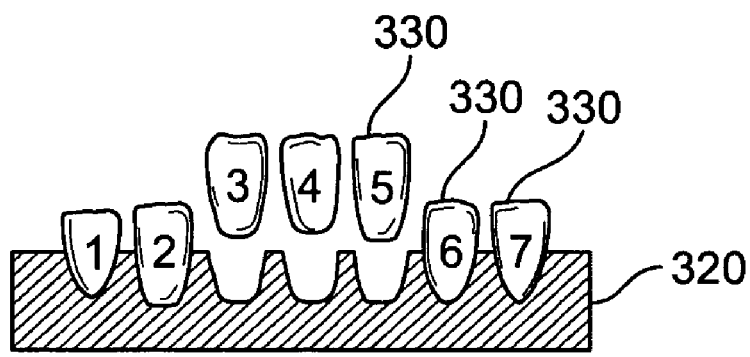

As shown in FIG. 3B, one or more teeth 330, in this case the teeth labeled 3, 4 and 5, may be separated from the base 320. The separated teeth 330 are those that the user desires to move in the patient during one stage of a treatment. In any given stage, one tooth 330 may be moved or multiple teeth 330 may be moved. Some teeth 330 that are moved in one stage may not be moved in another stage of treatment, while teeth 330 not moved in an earlier stage may be moved in a later stage. Any desired combination of tooth movements may be used. In some instances, one or more teeth 330 may be reshaped, such as by filing down a tooth, to facilitate tooth movements and avoid collision. As already mentioned, and as described further in the incorporated patents, tooth movements, reshaping and the like may be planned using a computer and treatment planning software.

Figure 3C:
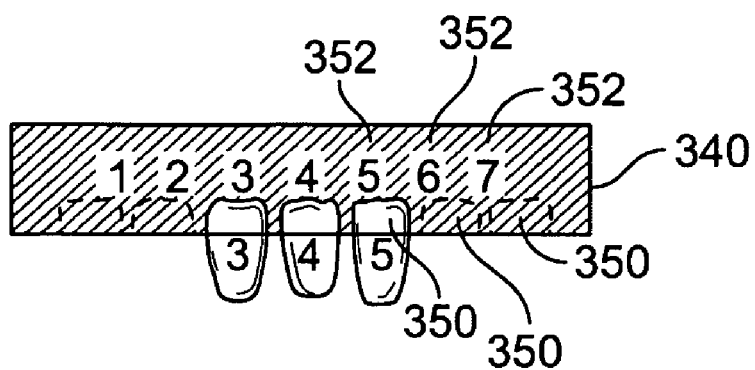

In FIG. 3C, the separated teeth 330 (3, 4, 5) are placed into corresponding recesses 350 in a guide 340. Each recess 350 is designated with a numerical marking 352 (or other marking in alternative embodiments) to alert a user as to which tooth 330 fits within each recess 350. The recesses are configured to place one or more of the patient's teeth in a slightly different configuration, compared to an original or earlier intermediate configuration.

Figure 3D:
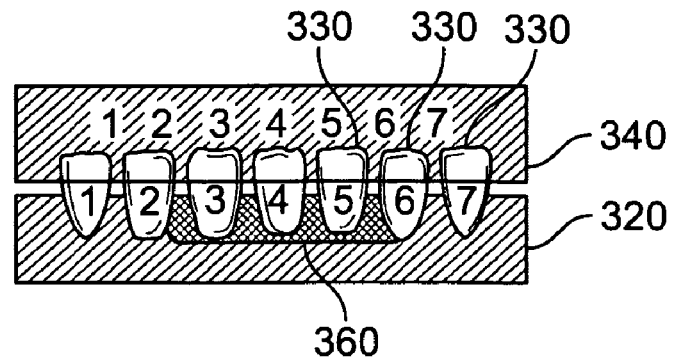
Figure 3E:
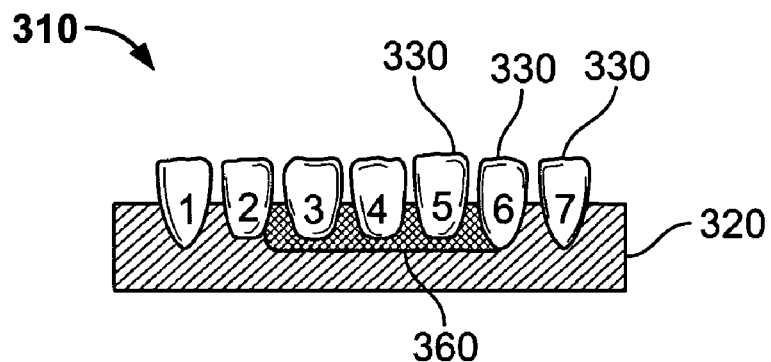

Once the separated teeth 330 are placed within their corresponding recesses 350, the rest of the model 310, with its remaining teeth 330, may be placed in the guide 340, as shown in FIG. 3D. The separated teeth 330 are then reattached to the model with holding compound 360, other adhesive material and/or any other suitable attachment mechanism. The reattached teeth 330 will then be in new positions relative to the model base 320, relative to their positions in FIG. 3A. After the teeth 330 are attached the guide 340 is removed, as shown in FIG. 3E, leaving the model 310 with reattached teeth 330. At this point, a duplicate model may be made, and an appliance may be made from the duplicate model. Alternatively, an appliance may be made directly from the model 310.

Figure 4A:
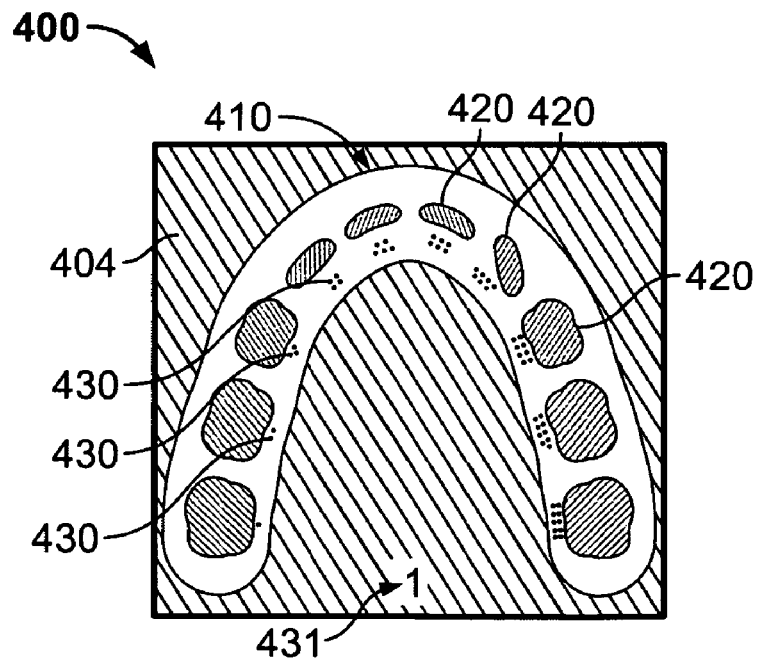
FIGS. 4A-4C are top views of a series of guides for positioning teeth on a tooth model, according to one embodiment of the present invention.
Figure 4B:
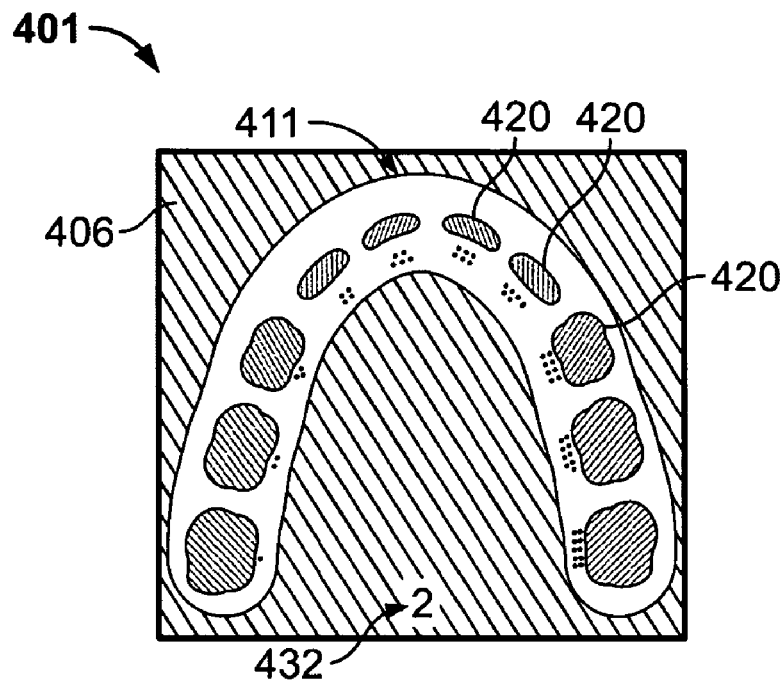
Figure 4C:
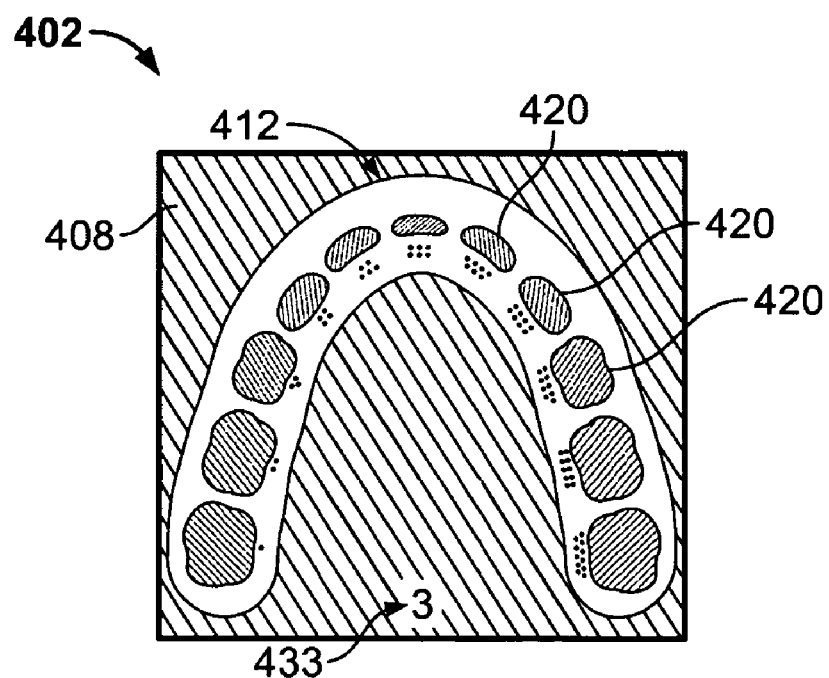

Referring now to FIGS. 4A-4C, one embodiment of a series of guides 400, 401, 402 is shown in top view. In this embodiment, each guide 400, 401, 402 is formed from a block 404, 406, 408 of material, such as a polymer or other suitable material. A line or indentation 410, 411, 412 in each block may optionally be included to show approximately an upper or lower arch shape in which the patient's teeth are located. In this embodiment, a CNC milling machine may be used to mill the guides 400, 401, 402 in the blocks of material 404, 406, 408. In alternative embodiments, each guide 400, 401, 402 may be formed using stereolithography or a similar rapid prototyping process to have an overall shape designated by the arch-shaped lines 410, 411, 412. The guides 400, 401, 402 each include multiple recesses 420 (or cavities), for receiving teeth from a tooth model. Each recess 420 is labeled with a number 430 or other marking which corresponds to markings on teeth from the tooth model. Each guide 400, 401, 402 also includes one or more markings 431, 432, 433 to designate its position in the series of guides. As shown in FIGS. 4A-4C, each guide 400, 401, 402 subtly repositions one or more of the teeth of a model, relative to one of the previous guides or to a patient's initial tooth position.

In the embodiment shown in FIGS. 4A-4C, the guides 400, 401, 402 are configured as bite registration or bite configuration guides. In other words, each guide 400, 401, 402 represents a bite pattern of upper or lower teeth, and the teeth of a model fit into each guide 400, 401, 402 as if they were biting into the guide.

Figure 5:
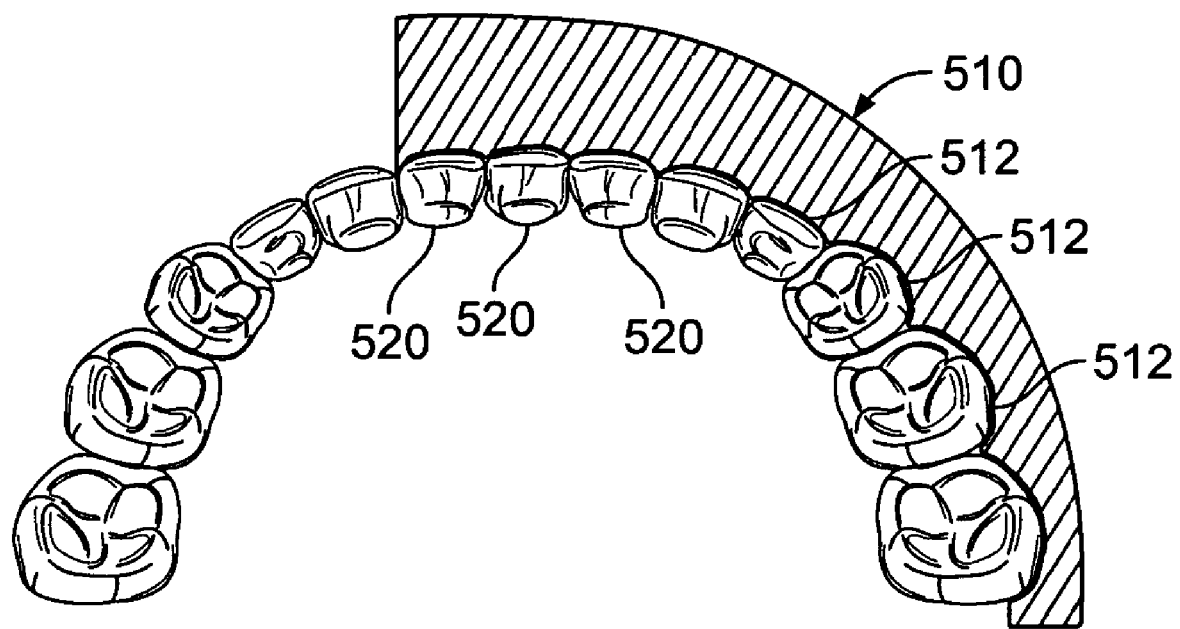
FIG. 5 is a top view of a guide for positioning teeth on a tooth model, according to one embodiment of the present invention.

With reference now to FIG. 5, an alternative embodiment of a guide 510 comprises a facial/buccal surface guide having multiple recesses 512 to receive facial and buccal surfaces of teeth 520. In other words, the teeth 520 of a model do not "bite into" the guide 510, but instead their facially-facing or buccally-facing surfaces fit against/into the guide 510. As demonstrated in FIG. 5, in some embodiments the guide 510 may be configured to fit only some of the teeth 520 of a patient's tooth model, rather than an entire upper or lower set of teeth. For example, if only a few teeth in the same area of the patient's upper or lower set of teeth are to be moved, it may be more convenient and/or less expensive to provide one or more sets of partial guides for manipulating portions of the patient's tooth models. In various alternative embodiments, guides 510 may include facial, buccal or lingual surface guides or bite configuration guides, or some combination thereof, and also may include any suitable combination of partial and/or complete guides.

Although the invention has been described fully above, a number of variations and alterations could be made within the scope of the present invention. For example, in alternative embodiments, steps in the various described methods for manipulating models and making tooth moving appliances may be carried out in different orders or skipped altogether, and in other embodiments, additional optional steps may be added or one or more steps may be altered. Therefore, the foregoing description of exemplary embodiments should not be interpreted to limit the scope of the invention described by the following claims.

What is claimed is:

1. A method for manipulating a three-dimensional model of a patient's teeth for making one or more tooth positioning appliances, the method comprising:

forming at least one three-dimensional model of the patient's teeth;

acquiring an initial digital data set representing at least part of the three-dimensional model;

manipulating a digital model derived from the initial digital data set to move at least one tooth from an initial position to a first intermediate position;

forming a first guide from the digital model with the at least one tooth in the first intermediate position;

separating the at least one tooth from the three-dimensional model;

placing the at least one tooth in the first guide in the first intermediate position; and securing the at least one tooth to the three-dimensional model in the first intermediate position.

2. The method of claim 1, wherein the at least one three-dimensional model comprises at least one of a model of the patient's upper teeth, a model of the patient's lower teeth, and a bite registration model.

3. The method of claim 1, wherein forming the at least one three-dimensional model comprises:
taking at least one impression of the patient's upper teeth, lower teeth, or both;
depositing a material into the impression;
allowing the material to harden to form the three-dimensional model; and
removing the three-dimensional model from the impression.

4. The method of claim 3, wherein depositing the material comprises depositing at least one of plaster, stone, plastic and polymer material into the impression.

5. The method of claim 1, wherein acquiring the initial digital data set comprises scanning at least one of the three-dimensional model, the patient's teeth and an impression of the patient's teeth to produce one or more digital scans.

6. The method of claim 1, wherein acquiring the initial digital data set comprises receiving one or more digital scans from a third party source.

7. The method of claim 5 or 6, wherein the digital scan(s) are acquired using a scanner selected from the group consisting of computed tomography, magnetic resonance imaging, X-ray, laser, structured light, spectral light and destructive scanners.

8. The method of claim 1, wherein manipulating the digital model comprises moving a plurality of teeth from initial positions to first intermediate positions.

9. The method as in claim 1, further comprising reshaping the at least one tooth on the digital model to facilitate repositioning of the tooth.

10. The method of claim 1, wherein forming the first guide comprises using a computer to direct a fabricating machine to form the guide, based on the manipulated digital model.

11. The method of claim 10, wherein using the computer to direct the fabricating machine comprises directing a milling machine to mill a plurality of recesses into a piece of material, each recess formed to receive at least a portion of a tooth of the three-dimensional model.

12. The method of claim 10, wherein using the computer to direct the fabricating machine comprises directing a rapid prototyping machine to build up the guide from a material, the guide having a plurality of recesses, each recess formed to receive at least a portion of a tooth of the three-dimensional model.

13. The method of claim 12, wherein the rapid prototyping machine is selected from the group consisting of stereolithography, laminate object manufacturing and fused deposition modeling machines.

14. The method of claim 1, wherein at least one of the separating, placing and securing steps are performed by a robot or other automated machine.

15. The method of claim 14, further comprising:
placing at least one reference jig on the three-dimensional model after the forming step; and
removably attaching the three-dimensional model to an automated cutting machine, using the jig as a reference, wherein the cutting machine then performs the separating step.

16. The method of claim 15, further comprising removably attaching the three-dimensional model to an automated tooth placing machine, using the jig as a reference, wherein the tooth placing machine then performs the placing step.

17. The method of claim 1, wherein securing the at least one tooth comprises applying at least one of wax, adhesive, resin, silicone and stone compounds.

18. The method of claim 1, wherein the at least one tooth comprises a plurality of teeth, the method further comprising labeling the teeth that are separated from the three-dimensional model to indicate positions in which they should be placed in the guide.

19. The method of claim 18, further comprising marking the guide to match each labeled tooth with a corresponding position in the guide.

20. The method of claim 1, further comprising reducing the size of the at least one tooth separated from the three-dimensional model to facilitate repositioning of the tooth.

21. The method of claim 1, further comprising placing one or more grooves or other surface markings on the at least one separated tooth to facilitate the securing step.

22. The method of claim 21, further comprising placing one or more additional grooves or other surface markings on the three-dimensional model to further facilitate the securing step.

23. The method of claim 1, further comprising:
removing the three-dimensional model from the guide with the at least one tooth secured to it in the first intermediate position; and
forming a first tooth positioning appliance over the three-dimensional model.

24. The method of claim 23, further comprising, after the removing step, forming a first intermediate model from the three-dimensional model, wherein the first tooth positioning appliance is formed over the first intermediate model.

25. The method of claim 23 or 24, wherein forming the first tooth positioning appliance comprises thermoforming a plastic material over the three-dimensional model or first intermediate model.

26. The method of claim 1, further comprising:
manipulating the digital model to move the at least one tooth from the first intermediate position to a second intermediate position;
forming a second guide from the digital model with the at least one tooth in the second intermediate position;
separating the at least one tooth from the three-dimensional model;
placing the at least one tooth in the guide in the second intermediate position; and
securing the at least one tooth to the three-dimensional model in the second intermediate position.

27. The method of claim 26, further comprising:
forming a first tooth positioning appliance over the three-dimensional model after the first securing step; and
forming a second tooth positioning appliance over the three-dimensional model after the second securing step.

28. The method of claim 26, further comprising:
forming, after the first securing step, a first intermediate model from the three-dimensional model; and
forming, after the second securing step, a second intermediate model from the three-dimensional model.

29. The method of claim 28, further comprising forming first and second tooth positioning appliances over the first and second intermediate models.

30. The method of claim 26, further comprising:
manipulating the digital model to move the at least one tooth from the second intermediate position to a third position;

forming a third guide from the digital model with the at least one tooth in the final position;

separating the at least one tooth from the three-dimensional model;

placing the at least one tooth in the guide in the third position; and securing the at least one tooth to the three-dimensional model in the third position.

31. The method of claim 30, further comprising:

forming a first tooth positioning appliance over the three-dimensional model after the first securing step;

forming a second tooth positioning appliance over the three-dimensional model after the second securing step; and forming a third tooth positioning appliance over the three-dimensional model after the third securing step.

32. The method of claim 30, further comprising:

forming, after the first securing step, a first intermediate model from the three-dimensional model;

forming, after the second securing step, a second intermediate model from the three-dimensional model; and forming, after the third securing step, a third tooth positioning appliance over the three-dimensional model.

33. The method of claim 32, further comprising forming first, second and third tooth positioning appliances over the first, second and third models.

34. The method of claim 31 or 33, wherein the third positioning appliance comprises a final appliance.

35. The method of claim 31 or 33, further comprising repeating the manipulating, forming, separating, placing and securing steps to form a fourth guide and fourth tooth positioning appliance.

36. The method of claim 35, further comprising repeating the manipulating, forming, separating, placing and securing steps to form between five and thirty guides and between five and thirty tooth positioning appliances.

37. The method of claim 1, further comprising:

manipulating the digital model to move at least one additional tooth from an initial position to a first intermediate position;

forming a second guide from the digital model with the at least one additional tooth in its first intermediate position;

separating the at least one additional tooth from the three-dimensional model;

placing the at least one additional tooth in the guide in its first intermediate position; and securing the at least one additional tooth to the three-dimensional model in its first intermediate position.

38. The method of claim 37, further comprising:

forming a first tooth positioning appliance over the three-dimensional model after the first securing step; and forming a second tooth positioning appliance over the three-dimensional model after the second securing step.

39. The method of claim 37, further comprising:

forming, after the first securing step, a first intermediate model from the three-dimensional model; and forming, after the second securing step, a second intermediate model from the three-dimensional model.

40. The method of claim 39, further comprising forming first and second tooth positioning appliances over the first and second models.

41. The method of claim 1, wherein the first guide is formed to be configured to receive the at least one moved tooth and at least one other tooth of the three dimensional model, so as to reposition the at least one tooth to the first intermediate position relative to the three-dimensional model.

42. The method of claim 41, further comprising:

manipulating the digital model to move the at least one tooth from the first intermediate position to a second position; and forming a second guide from the digital model, wherein the second guide is configured to receive the at least one moved tooth and at least one other tooth of the three-dimensional model so as to reposition the at least one tooth to the second position relative to the three-dimensional model.

43. The method of claim 41, wherein the first guide is formed to include a plurality of recesses, each recess shaped to receive at least a portion of a tooth of the model, wherein at least one of the recesses is shaped to reposition a tooth separated from the model from an initial position to a first position, and wherein the at least one recess shaped to reposition the tooth is shaped according to instructions from a manipulated digital model of the patient's teeth.

44. The method of claim 43, wherein the first guide comprises a three-dimensional bite pattern guide representing a bite pattern of a set of teeth selected from the group consisting of the patient's upper set of teeth and the patient's lower set of teeth.

45. The method of claim 43, wherein a plurality of the recesses are shaped to reposition a plurality of teeth on the three-dimensional model, each recess configured to reposition one of the teeth.

46. A method for making a tooth positioning appliance for repositioning a patient's teeth, the method comprising:

forming a first guide from a digital model of the patient's teeth;

separating at least one tooth from a three-dimensional model of the patient's teeth;

placing the at least one tooth in the first guide, wherein the first guide repositions the at least one tooth relative to the rest of the three-dimensional model from an initial position to a first position;

securing the at least one tooth to the three-dimensional model in the first intermediate position; and forming a first tooth positioning appliance over the three-dimensional model with the at least one tooth in the first position.

47. The method of claim 46, wherein the at least one tooth comprises a plurality of teeth.

48. The method of claim 46, further comprising:

forming a second guide from the digital model of the patient's teeth;

separating the at least one tooth from the three-dimensional model;

placing the at least one tooth in the second guide, wherein the second guide repositions the at least one tooth to a second position;

securing the at least one tooth to the three-dimensional model in the second position; and forming a second tooth positioning appliance over the three-dimensional model with the at least one tooth in the second position.

49. The method of claim 48, further comprising repeating the forming, separating, placing, securing and forming steps to provide a third guide and a third tooth positioning appliance.

50. The method of claim 49, further comprising repeating the forming, separating, placing, securing and forming steps to provide between four and thirty guides and between four and thirty tooth positioning appliances.

51. The method of claim 48, further comprising, before forming the appliances:
forming a first intermediate model from the three-dimensional model with the at least one tooth in the first position;
forming a second intermediate model from the three-dimensional model with the at least one tooth in the second position,
wherein the first and second tooth positioning appliances are formed over the first and second intermediate models.

52. The method of claim 46, wherein at least one of the separating, placing and securing steps are performed by a robot or other automated machine.

53. The method of claim 52, wherein the separating step is performed by an automated machine selected from the group consisting of a laser cutting machine and a computer numerical control (CNC) machine.

54. The method of claim 52, further comprising trimming material from the appliances to create finished appliances, wherein the material is trimmed using an automated machine directed according to one or more digital data sets.

55. The method of claim 46, further comprising:
forming a second guide from the digital model of the patient's teeth;
separating the at least one tooth from the three-dimensional model;
placing the at least one tooth in the second guide, wherein the second guide repositions at least one additional tooth to a first position from an initial position;
securing the at least one additional tooth to the three-dimensional model in the first position; and
forming a second tooth positioning appliance over the three-dimensional model with the at least one additional tooth in the first position.

56. The method of claim 55, further comprising, before forming the appliances:
forming a first intermediate model from the three-dimensional model with the at least one tooth in the first position;
forming a second intermediate model from the three-dimensional model with the at least one additional tooth in the first position,
wherein the first and second tooth positioning appliances are formed over the first and second intermediate models.

57. The method of claim 46, where the step of forming a first guide comprises:
forming the three-dimensional model of the patient's teeth;
acquiring an initial digital data set representing at least part of the three-dimensional model;
manipulating a digital model derived from the initial digital data set to move at least one tooth from an initial position to a first position; and
forming a first guide from the digital model, wherein the first guide is configured to receive the at least one moved tooth and at least one other tooth of the three dimensional model so as to reposition the at least one tooth to the first position relative to the three-dimensional model.

58. The method of claim 57, further comprising:
manipulating the digital model to move the at least one tooth from the first position to a second position; and
forming a second guide from the digital model, wherein the second guide is configured to receive the at least one moved tooth and at least one other tooth of the three-dimensional model so as to reposition the at least one tooth to the second position relative to the three-dimensional model.

59. The method of claim 57, further comprising:
manipulating the digital model to move at least one additional tooth from an initial position to a first position; and
forming a second guide from the digital model, wherein the second guide is configured to receive the at least one additional moved tooth and at least one other tooth of the three-dimensional model so as to reposition the at least one tooth to the first position relative to the three-dimensional model.

60. A method for making a plurality of tooth positioning appliances for repositioning a patient's teeth, the method comprising:
providing a series of guide-forming tooth models, based on a series of digital data sets derived from the patient's teeth;
forming a series of guides from the guide-forming models;
separating at least one tooth from a 3D model of the patient's teeth;
placing the at least one tooth in a first guide of the set of guides, wherein the first guide repositions the at least one tooth relative to the rest of the 3D model from an initial position to a first position;
securing the at least one tooth to the 3D model in the first intermediate position;
forming a first tooth positioning appliance over the 3D model with the at least one tooth in the first position; and
repeating the separating, placing, securing and forming steps as many times as desired to provide a plurality of appliances.

* * * * *